US009646134B2

(12) United States Patent
Sanborn et al.

(10) Patent No.: US 9,646,134 B2
(45) Date of Patent: *May 9, 2017

(54) BAMBAM: PARALLEL COMPARATIVE ANALYSIS OF HIGH-THROUGHPUT SEQUENCING DATA

(75) Inventors: John Zachary Sanborn, Santa Cruz, CA (US); David Haussler, Santa Cruz, CA (US)

(73) Assignee: The Regents of the University of California, Oakland, CA (US)

(*) Notice: Subject to any disclaimer, the term of this patent is extended or adjusted under 35 U.S.C. 154(b) by 698 days.

This patent is subject to a terminal disclaimer.

(21) Appl. No.: 13/373,550

(22) Filed: Nov. 18, 2011

(65) Prior Publication Data
US 2012/0066001 A1    Mar. 15, 2012

Related U.S. Application Data

(63) Continuation-in-part of application No. 13/134,047, filed on May 25, 2011.
(Continued)

(51) Int. Cl.
*G06F 19/22* (2011.01)
*G06F 19/20* (2011.01)
(Continued)

(52) U.S. Cl.
CPC .......... *G06F 19/22* (2013.01); *G06F 3/04845* (2013.01); *G06F 17/241* (2013.01); *G06F 19/18* (2013.01); *G06F 19/28* (2013.01); *G06F 19/345* (2013.01); *G06N 7/005* (2013.01); *G06Q 50/24* (2013.01)

(58) Field of Classification Search
CPC ........ G06Q 50/22; G06Q 50/24; G06F 19/18; G06F 19/22; G06F 19/24; G06F 19/322; G06F 19/345
See application file for complete search history.

(56) References Cited

U.S. PATENT DOCUMENTS 4,736,866 A    4/1988 Leder et al.
5,175,383 A    12/1992 Leder et al.
(Continued)

FOREIGN PATENT DOCUMENTS

JP    2003099440    4/2003
JP    2003527855    9/2003
(Continued)

OTHER PUBLICATIONS

Quinlan, Aaron R., and Ira M. Hall. "BEDTools: a flexible suite of utilities for comparing genomic features." Bioinformatics 26.6 (2010): 841-842.*
(Continued)

*Primary Examiner* — Neha Patel
*Assistant Examiner* — Jonathan Durant
(74) *Attorney, Agent, or Firm* — Womble Carlyle Sandridge & Rice LLP

(57) ABSTRACT

A differential sequence object is constructed on the basis of alignment of sub-strings via incremental synchronization of sequence strings using known positions of the sub-strings relative to a reference genome sequence. An output file is then generated that comprises only relevant changes with respect to the reference genome.

31 Claims, 5 Drawing Sheets

Related U.S. Application Data

(60) Provisional application No. 61/396,356, filed on May 25, 2010.

(51) Int. Cl.
| | | |
|---|---|---|
| *G06F 17/24* | (2006.01) | |
| *G06N 7/00* | (2006.01) | |
| *G06F 3/0484* | (2013.01) | |
| *G06F 19/00* | (2011.01) | |
| *G06F 19/28* | (2011.01) | |
| *G06F 19/18* | (2011.01) | |
| *G06Q 50/24* | (2012.01) | |

(56) References Cited

U.S. PATENT DOCUMENTS

| | | | |
|---|---|---|---|
| 5,767,337 | A | 6/1998 | Roses et al. |
| 6,346,381 | B1 | 2/2002 | Cohen |
| 6,355,423 | B1 | 3/2002 | Rothberg et al. |
| 6,982,145 | B1 | 1/2006 | Mercola et al. |
| 7,700,359 | B2 | 4/2010 | Chan |
| 8,140,270 | B2 | 3/2012 | Kingsmore |
| 8,340,914 | B2 | 12/2012 | Gatewood et al. |
| 8,700,430 | B2 | 4/2014 | Miller et al. |
| 8,751,100 | B2 | 6/2014 | Johnson |
| 9,092,401 | B2 | 7/2015 | Richards |
| 9,165,109 | B2 | 10/2015 | Chaisson |
| 2003/0003463 | A1 | 1/2003 | Rothberg et al. |
| 2003/0180717 | A1 | 9/2003 | Esteban |
| 2004/0015298 | A1 | 1/2004 | Swindells et al. |
| 2004/0153255 | A1* | 8/2004 | Ahn ................................ 702/20 |
| 2005/0079504 | A1 | 4/2005 | Amitai et al. |
| 2007/0178474 | A1 | 8/2007 | Cracauer et al. |
| 2008/0077607 | A1* | 3/2008 | Gatewood et al. ............ 707/101 |
| 2008/0126117 | A1* | 5/2008 | Miller et al. ....................... 705/2 |
| 2011/0098193 | A1 | 4/2011 | Kingsmore |
| 2012/0059670 | A1 | 3/2012 | Sanborn |
| 2012/0066001 | A1 | 3/2012 | Sanborn |
| 2013/0073217 | A1 | 3/2013 | Dewey |
| 2014/0287934 | A1 | 9/2014 | Szelinger |
| 2014/0371109 | A1 | 12/2014 | McMillen |
| 2015/0141391 | A1 | 5/2015 | Chinnaiyan |
| 2016/0180019 | A1 | 6/2016 | van Rooyen |
| 2016/0306922 | A1 | 10/2016 | van Rooyen |
| 2016/0306923 | A1 | 10/2016 | van Rooyen |

FOREIGN PATENT DOCUMENTS

| | | |
|---|---|---|
| JP | 2004501669 | 1/2004 |
| JP | 2008526775 | 7/2008 |
| JP | 2010204838 | 9/2010 |
| KR | 20040031291 | 4/2004 |
| KR | 2004-0070438 | 8/2004 |

OTHER PUBLICATIONS

Wheeler, David A., et al. "The complete genome of an individual by massively parallel DNA sequencing." Nature 452.7189 (2008): 872-876.*

Kraus, Matthias H., Yasuhito Yuasa, and Stuart A. Aaronson. "A position 12-activated H-ras oncogene in all HS578T mammary carcinosarcoma cells but not normal mammary cells of the same patient." Proceedings of the National Academy of Sciences 81.17 (1984): 5384-5388.*

Choi, Murim, et al. "Genetic diagnosis by whole exome capture and massively parallel DNA sequencing." Proceedings of the National Academy of Sciences 106.45 (2009): 19096-19101.*

Li, Heng, et al. "The sequence alignment/map format and SAMtools." Bioinformatics 25.16 (2009): 2078-2079.*

Mariadason, John M., Georgia A. Corner, and Leonard H. Augenlicht. "Genetic reprogramming in pathways of colonic cell maturation induced by short chain fatty acids: comparison with trichostatin A, sulindac, and curcumin and implications for chemoprevention of colon cancer." Cancer research 60.16 (2000): 4561-4572.*

Zhu, Jingchun, et al. "Comparative genomics search for losses of long-established genes on the human lineage." PLoS computational biology 3.12 (2007): e247.*

Dean, Michael, et al. "Genetic restriction of HIV-1 infection and progression to AIDS by a deletion allele of the CKR5 structural gene." Science 273.5283 (1996): 1856-1862.*

Flicek, Paul, and Ewan Birney. "Sense from sequence reads: methods for alignment and assembly." Nature Methods 6 (2009): S6-S12.*

Giardine, Belinda, et al. "Galaxy: a platform for interactive large-scale genome analysis." Genome research 15.10 (2005): 1451-1455.*

Karolchik, Donna, Angie S. Hinrichs, and W. James Kent. "The UCSC genome browser." Current protocols in bioinformatics (2009): 1-4.*

Kuhn, R. M., et al. "The UCSC genome browser database: update 2009." Nucleic acids research 37.suppl 1 (2009): D755-D761.*

Rhead, Brooke, et al. "The UCSC genome browser database: update 2010." Nucleic acids research 38.suppl 1 (2010): D613-D619.*

Li, Heng, Jue Ruan, and Richard Durbin. Mapping short DNA sequencing reads and calling variants using mapping quality scores. Genome research 18.11 (2008) 1851-1858.*

Quinlan, Aaron R., and Ira M. Hall. "BEDTools: a flexible suite of utilities for comparing genomic features." Bioinformatics 26.6 (2010) 841-842.

Kraus, Matthias H., Yasuhito Yuasa, and Stuart A. Aaronson. "A position 12-activated H-ras oncogene in all HS578T mammary carcinosarcoma cells but not normal mammary cells of the same patient." Proceedings of the National Academy of Sciences 81.17 (1984): 5384-5388.

Dean, Michael, et al. "Genetic restriction of HIV-1 infection and progression to AIDS by a deletion allele of the CKR5 structural gene." Science 273.6283 (1996): 1856-1862.

Flicek, Paul, and Ewan Birney, "Sense from sequence reads: methods for alignment and assembly," Nature Methods 6 (2009): S6-S12.

Giardine, Belinda, et al. "Galaxy: a platform for interactive large-scale genome analysis." Genome research 15.10 (2005) 1451-1455.

Rhead, Brooke, et al. "The UCSC genome browser database: update 2010." Nucleic acids research 38.suppl 1 (2010): D619.

lriternationai Search Report, PCT/US2011/001996 mailed Oct. 4, 2012.

U.S. Appl. No. 13/134,047, filed May 25, 2011, Bambam: Parellel Comparative Analysis of High Throughput Sequencing Data, J. Zachary Sanborn.

U.S. Appl. No. 13/373,550, filed Nov. 18, 2011, Parallel Comparative Analysis of High Throughput Sequencing Data, J. Zachary Sanborn.

Li, Heng, et al.: "A survey of sequence alignment algorithms for next-generation sequencing", Briefings in Bioinformatics, vol. 11, No. 5, pp. 473-483. May 11, 2010.

Thompsons, et al.; "A Comprehensive Comparison of Multiple Sequence Alignment Programs", 1999, Nucleic Acids Research, vol. 27 No. 13, pp. 2682-2690.

Japanese Patent Office, Office Action for Japanese Patent Application 2013-512603, mailed Jun. 4, 2015.

Robinson et al.; "Integrative genomics viewer", Nature Biotechnology, vol. 29, No. 1, Jan. 2011, pp. 24-26. Published with references to supplemental information, retrieved from [http://www.nature.com/nbt/journal/v29/n1/full/nbt.1754.html] on [Jan. 4, 2017], 83 pages.

Krzywinski et al.; "Circos: an Information Aesthetic for Comparative Genomics", Genome Res. published online Jun. 18, 2009. doi:10.1101/gr.092759.109. Retrieved from [genome.cshlp.org] on [Jan. 4, 2017] 25 pages.

Edmonson et al.; "Bambino: a varient detector and alignment viewer for next-generation sequencing data in the 4 SAM/BAM format", Jan. 28, 2011. Bioinformatics, vol. 27, No. 6, 2011, pp. 865-866. doi:10.1093/bioinformatics/btr032.

(56) References Cited

OTHER PUBLICATIONS

Carver et al.; "BamView: viewing mapped read alignment data in the context of the reference sequence." Bioinformatics, Jan. 12, 2010, vol. 26, No. 5 2010, pp. 676-677. doi:10.1093/bioinformatics/btq010.
Popova et al.; "Genome Alteration Print (GAP): a tool to visualize and mine complex cancer genome profiles obtained by SNP arrays." Published Nov. 11, 2009. Genome Biology 2009, 10:R128 (doi:10.1186/gb-2009-10-11-r128). 14 pages.
Stratton, et al., The Cancer Genome, Nature vol. 458, pp. 719-724 (2009).
Sjoblom, et al., The Consensus coding Sequences of Human Breast and Colorectal Cancers, Science vol. 314, pp. 268-274 and Supporting Online Material (2006).

* cited by examiner

BAMBAM: PARALLEL COMPARATIVE ANALYSIS OF HIGH-THROUGHPUT SEQUENCING DATA

This application is a continuation-in-part application of U.S. Non-Provisional patent application Ser. No. 13/134,047 entitled "Bambam: Parallel Comparative Analysis Of High-Throughput Sequencing Data" filed 25 May 2011, which is incorporated by reference herein, and which is related to and claims priority from U.S. Provisional Patent Application Ser. No. 61/396,356 entitled "Bambam: Parallel Comparative Analysis Of High-Throughput Sequencing Data" filed 25 May 2010, both of which are herein incorporated by reference in their entirety.

This invention was made with government support under 1U24CA143858-01 awarded by the National Cancer Institute. The government has certain rights to this invention.

FIELD OF THE INVENTION

The field of the invention is computational biology, especially as it relates to comparative analysis of genomic data to produce a differential genetic sequence object.

BACKGROUND OF THE INVENTION

Recent advances in sequencing had led to a wealth of genomic and sub-genomic data for both individual organisms and tissues of an organism as well as for distinct populations and even species. This has spurred the development of genome-based personalized treatment or diagnosis of various diseases, prognosis/risk assessment, and even treatment response prediction using genomic, transcriptional, and/or epigenetic information.

As the amount of genomic data has reached significant levels, computational requirement and manners of meaningful output generation have become challenging. For example, multiple tumor and matched normal whole genome sequences are now available from projects like 'The Cancer Genome Atlas' (TCGA) and extraction of relevant information is difficult. This is further compounded by the need for high genome sequencing coverage (for example, greater than 30-fold) to so obtain statistically relevant data. Even in compressed form, genomic information can be often reach hundreds of gigabytes, and an analysis comparing multiple of such large datasets is in most cases slow and difficult to manage, however, absolutely necessary in order to discover the many genomic changes that occurred in any given sample relative to a second sample.

Therefore, even though numerous systems and methods of comparative genomic analysis known in the art, all or all of them suffer from one or more disadvantage. Consequently, there is still a need for improved systems and methods of comparative genomic analysis.

SUMMARY OF THE INVENTION

The inventors have discovered various systems and methods of comparative genomic analysis that allow for rapid generation of a meaningful output in a manner that does not require multiple massive files to be processed and in a manner that avoids generation of similarly massive output files with a relatively low information density with respect to genomic aberrations.

In one aspect of the inventive subject matter, a method of deriving a differential genetic sequence object includes a step of providing access to a genetic database that stores (a) a first genetic sequence string representing a first tissue and (b) a second genetic sequence string representing a second tissue, wherein the first and second sequence strings have a plurality of corresponding sub-strings. In another step, access is provided to a sequence analysis engine that is coupled with the genetic database, and in yet another step the sequence analysis engine produces a local alignment by incrementally synchronizing the first and second sequence strings using a known position of at least one of plurality of corresponding sub-strings. In a further step, the sequence analysis engine uses the local alignment to generate a local differential string between the first and second sequence strings within the local alignment; and the sequence analysis engine uses the local differential string to update a differential genetic sequence object in a differential sequence database.

Most preferably, the first and second genetic sequence strings represent at least 10%, and more typically at least 50% of a genome, transcriptome, or proteome of the first and second tissues, or even substantially the entire genome, transcriptome, or proteome of the first and second tissues, respectively. It should further be appreciated that the first and second tissues originate from the same biological entity (for example, a patient, a healthy individual, a cell line, a stem cell, an experimental animal model, a recombinant bacterial cell, or a virus). On the other hand, the first tissue may be a healthy tissue while the second may be a diseased tissue (for example, a tumor tissue). In further contemplated aspects, the corresponding sub-strings comprise homozygous or heterozygous alleles.

It is also generally preferred that the step of synchronizing comprises aligning at least one of the plurality of sub-strings wherein the alignment is based on an a priori known location within the first string. Alternatively or additionally, the step of synchronizing comprises aligning at least one of the plurality of sub-strings based on a known reference string (for example, consensus sequence) that includes known locations for the at least one of the plurality of sub-strings, and/or the step of synchronizing comprises aligning the at least one of the plurality of sub-strings within a window having a length of less than a length of the at least one of the plurality of sub-strings. Where desired, contemplated methods may additionally include a step of iteratively incrementally synchronizing the first and second sequence strings throughout the entire length of the first sequence string.

In especially preferred methods, the differential genetic sequence object represents a plurality of local differential strings for at least one chromosome, represents a plurality of local differential strings for substantially the entire genome of the first tissue, and/or comprises an attribute comprising metadata describing the differential genetic sequence object. Particularly preferred attributes are the state of at least one of the first and second tissues. For example, the state may include a physiological state (for example, neoplastic growth, apoptosis, state of differentiation, tissue age, and responsiveness to treatment) of at least one of the first and second tissues, or a genetic status (for example, ploidy, gene copy number, repeat copy number, inversion, deletion, insertion of viral genes, somatic mutation, germline mutation, structural rearrangement, transposition, and loss of heterozygosity). Suitable states also include pathway model information associated with a signaling pathway (for example, a growth factor signaling pathway, a transcription factor signaling pathway, an apoptosis pathway, a cell cycle pathway, and a hormone response pathway) within the tissues. It is still further contemplated that the genetic sequence object comprises a file, which most preferably conforms to a standardized format (for example, SAM/BAM format).

In another aspect of the inventive subject matter, the inventors also contemplate a method of providing a health care service. In such methods, access is provided to an analysis engine that is informationally coupled to a medical records storage device, wherein the storage device stores a differential genetic sequence object for a patient. In another step, the analysis engine produces a patient-specific data set using presence of a local differential string or constellation of a plurality of local differential strings in the differential genetic sequence object for the patient, and the analysis engine also produces a patient-specific instruction based on the patient-specific data set.

In particularly preferred methods the medical records storage device is configured as a smart-card and is carried by the patient, and/or is remotely accessible by a healthcare provider.

Most typically, the differential genetic sequence object for the patient comprises a plurality of local differential strings for at least two chromosomes, or even for substantially the entire genome of the patient. Alternatively, or additionally, the differential genetic sequence object for the patient may also comprise a plurality of local differential strings representing at least two tissue types, or at least two temporally spaced results for the same tissue (for example, the temporally spaced results for the same tissue are obtained from before and after commencement of a treatment). It is further generally preferred that the patient-specific instruction is a diagnosis, a prognosis, a prediction of treatment outcome, a recommendation for a treatment strategy, and/or a prescription.

In yet another aspect of the inventive subject matter, the inventors contemplate a method of analyzing a population that includes a step of obtaining and storing a plurality of differential genetic sequence objects in a medical records database of a population, wherein the records database is informationally coupled to an analysis engine. In another step, the analysis engine identifies a constellation of a plurality of local differential strings within the plurality of differential genetic sequence objects to produce a constellation record, and the analysis engine uses the constellation record to generate a population analysis record.

In such methods it is generally contemplated that the population comprises a plurality of blood relatives and/or a plurality of members characterized by sharing at least one common feature (for example, exposure to a pathogen, exposure to a noxious agent, health history, treatment history, treatment success, gender, species, and/or age). Suitable populations may also comprise a plurality of members characterized by sharing geographic location, ethnicity, and/or occupation. Thus, it should be recognize that the population analysis record comprises paternity or maternity confirmation.

It is further contemplated that the methods presented herein may further include a step of comparing a constellation record of an individual patient with the population analysis record, which may thus creates a patient-specific record (for example, indicating a risk assessment or an identification of the patient as belonging to a specified population). The patient-specific record may also comprise a diagnosis, a prognosis, a prediction of treatment outcome, a prescription, and/or a recommendation for a treatment strategy.

Consequently, the inventors also contemplate a method of analyzing a differential genetic sequence object of a person, in which in one step a reference differential genetic sequence object is stored in a medical records database that is informationally coupled to an analysis engine. The analysis engine then calculates a deviation between a plurality of local differential strings in the differential genetic sequence object of the person and a plurality of local differential strings in the reference differential genetic sequence object to produce a deviation record, and the analysis engine then uses the deviation record to generate a person-specific deviation profile.

In such methods, it is preferred that the reference differential genetic sequence object is calculated from a plurality of local differential strings of the person, or from a plurality of local differential strings of the person.

It should be recognized that in the methods presented herein the patient or person may be a patient or person diagnosed with a condition, and particularly a disease or a disorder. For example, contemplated conditions include acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermnatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, akathesia, Alzheimer's disease, amnesia, amyotrophic lateral sclerosis (ALS), ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

Further contemplated conditions also include cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and developmental disorders such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, sensorineural hearing loss, and any disorder associated with cell growth and differentiation, embryogenesis, and morphogenesis involving any tissue, organ, or system of a subject, for example, the brain, adrenal gland, kidney, skeletal or reproductive system.

Still further contemplated conditions include of endocrinological disorders such as disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; hyperpituitarism including acromegaly, giantism, and syndrome of inappropriate antidiuretic hormone (ADH) secretion (SIADH); and disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalemia); respiratory disorders such as allergy, asthma, acute and chronic inflammatory lung diseases, ARDS, emphysema, pulmonary congestion and edema, COPD, interstitial lung diseases, and lung cancers; cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
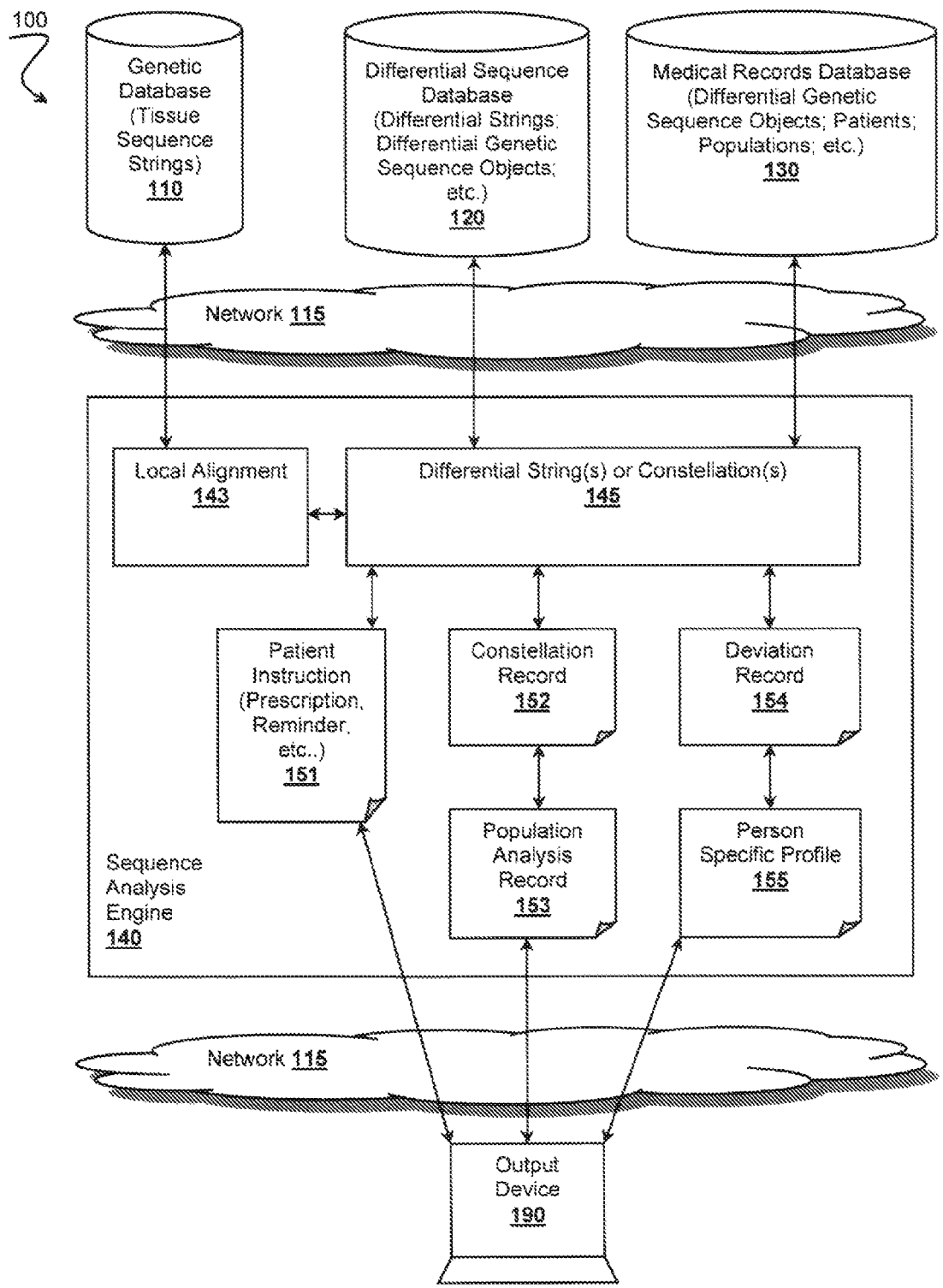
FIG. 1 is a schematic of an exemplary computer system to produce a differential genetic sequence object according to the inventive subject matter.

The inventors have developed systems and methods where multiple relatively small genomic sequence substrings (for example, short reads from sequencing runs) of respective larger genetic sequence strings from a first and second tissue sample (for example, healthy and diseased tissue) are obtained. The genetic sequence strings are then incrementally synchronized using one or more known positions of at least one of corresponding sub-strings to so produce a local alignment. The so generated local alignment is then analyzed (typically using a reference genomic sequence) to generate a local differential string between the first and second sequence strings within the local alignment that thus contains significant differential information (typically relative to the reference genomic sequence). A differential genetic sequence object for a portion or even the entire genome is then created using the local differential string, and most typically a plurality of local differential strings.

It should therefore be recognized that instead of processing two extremely large files to generate another extremely large intermediate (or even output) file, genome wide analysis can be achieved in multiple significantly smaller portions wherein the smaller portions are aligned to a reference genome using known positions within the genome of one or more sub-strings. Viewed from another angle, alignment is performed by incremental synchronization of sequence strings using known positions of substrings and a reference genome sequence, and an output file can be generated that comprises only relevant changes with respect to a reference genome. Thus, the processing speed is significantly improved and the amount of data required for production of a meaningful output is dramatically reduced. Still further, contemplated systems and methods further allow, inter alia, haplotyping/somatic and germline variant calling, and determination of allele-specific copy numbers. Moreover, the systems and methods presented herein are suitable for use with sequence information in SAM/BAM-format.

For example, multiple sequencing fragments (for example, short reads from a tumor sample of a donor and corresponding non-tumor sample of the same donor) are aligned to the same reference genome, which is employed to organize the sequencing fragments from the samples. BAM-BAM then uses two sequencing fragment datasets (one from the tumor, the other from corresponding normal "germline" tissue) from the same patient and the reference genome, and reads the datasets such that all sequences in both datasets overlapping the same genomic position (based on the reference genome and annotation in sub-strings) are processed at the same time. This is the most efficient method for processing such data, while also enabling complex analyses that would be difficult or impossible to accomplish in a serialized manner, where each dataset is processed by itself, and results are only merged afterwards.

Consequently, it should be recognized that BAMBAM incrementally reads from two files at the same time, constantly keeping each BAM file in synchrony with the other and piling up the genomic reads that overlap every common genomic location between the two files. For each pair of pileups, BAMBAM runs a series of analyses before discarding the pileups and moving to the next common genomic location. By processing tin this manner, the computer's RAM usage is dramatically reduced and processing speed is limited primarily by the speed that the file system can read the two files. This enables BAMBAM to process massive amounts of data quickly, while being flexible enough to run on a single computer or across a computer cluster. Another important benefit to processing these files with BAMBAM is that its output is fairly minimal, typically only including the important differences found in each file. This produces what is essentially a whole-genome differential analysis between the patient's tumor and germline genomes, requiring much less disk storage than it would take if all genome information was stored for each file separately.

It should be noted that while the following description is drawn to a computer/server based pathway analysis system, various alternative configurations are also deemed suitable and may employ various computing devices including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (for example, hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

Moreover, the following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the current document "coupled with" should also be construed to mean "communicatively coupled with".

Overview

FIG. 1 illustrates genetic sequence analysis ecosystem 100, which includes sequence analysis engine 140 coupled with one or more databases, possibly over network 115 (for example, LAN, WAN, VPN, Internet, etc.). Preferred databases include genetic database 110 storing genetic sequence strings for one or more tissues, differential sequence database 120 storing differential genetic sequence objects representing local differential strings, and medical records database 130 storing one or more medical records associated with a patient, person, population, or other type of entities. Medical records database 130 can also store one or more differential genetic sequence objects, possibly associated with patients, persons, populations or other groups.

One aspect of the inventive subject matter is considered to include management of differential genetic sequence objects. Through analysis of genetic sequence strings, analysis engine 140 can create differential strings or constellations of differential strings 145. Differential strings 145 can be converted to differential genetic sequence objects, which in turn can be stored in differential sequence database 120 or medical records database 130. The sequence objects can be tagged with one or more attributes describing the nature of the objects. Example attributes can include time stamps of object creation, time stamp of when sample was taken from a patient, patient name, demographic information, tissue type (for example, healthy, diseased, tumor, organ tissue, etc.), or other features. The attributes can by leveraged by analysis engine 140 to establish one or more correlations among characteristics associated with medical records in medical records database 130.

Management of differential genetic sequence objects covers a broad spectrum of roles or responsibilities. As discussed above, one aspect includes creation of such objects. Analysis engine 140 is also preferably configured to update, analyze, modify, track in time, delete, copy, split, append, or other wise manipulate the sequence objects as desired. Further, analysis engine 140 can provide a differential genetic sequence object management interface, possibly on output device 190. For example, in some embodiments, ecosystem 100 operates as a for-fee service comprising one or more web servers available over the Internet. In such an embodiment, a computer with a browser can interface with analysis engine 140 to manage or interact with the differential genetic sequence objects.

In some embodiments, as discussed further below, analysis engine 140 is configured to analyze genetic sequence strings obtained from genetic database 110. Preferably the genetic sequence strings are associated within at least two different tissue samples. Analysis engine 140 produces one or more local alignments 143 by incrementally synchronizing at least two sequences using at least a known position of corresponding sub-strings in the sequence strings. Further, analysis engine 140 uses the local alignment to generate one or more local differential strings 145 or constellations of differential strings 145 between the genetic sequence strings. Analysis engine 140 can then use the differential strings 145 to update differential genetic sequence objects in differential sequence database 120 or medical records database 130. The differential sequence objects can then be used for further analysis.

In some embodiments, analysis engine 140 communicatively couples with medical records database 130 that stores differential genetic sequence objects for specific patients, persons, individuals, families, populations, or other groups. Analysis engine 140 obtains a differential sequence object for a patient and produces a patient specific data set based on presence of a local differential string or constellation of differential string associated with the patient's sequence object. Then, analysis engine 140 can leverage the patient-specific data set to generate or otherwise produce one or more patient specific instructions 151. For example, through analysis of the patient's specific local differential strings, analysis engine 140 can determine if there is a correlation between the patient's specific differential strings and known conditions, which in turn can be mapped to instructions. Contemplated instructions can include a diagnosis, a prognosis, a recommended treatment, a prediction, a prescription, or other type of instructions.

In yet other embodiments, analysis engine 140 obtains differential genetic sequence objects stored in medical records database 130 where the sequence objects are associated with a population of individuals. The analysis engine 140 identifies a constellation of local differential strings from multiple sequence objects and generates constellation record 152 from the constellation. Constellation record 152 comprises a representation of information (for example, attributes, properties, metadata, characteristics, etc.) related to local differential strings associated with the population. Analysis engine 140 uses constellation records 152 to generated population analysis record 153. Thus, the differential genetic sequence objects can be mapped to population segments.

Still another embodiment includes analysis engine 140 using the differential genetic sequence object to determine an extent that a person's genetic sequence deviates from a reference sample. A reference differential genetic sequence object, possibly representing a real person or a canonical person, can be stored as a medical record in medical records database 130. Analysis engine 140 calculates a deviation between a person's local differential strings from different sequence objects associated with the person and the local differential strings from the reference differential genetic sequence object. Once the deviation is calculated, analysis engine 140 generates a deviation record 154 representing the deviation or departure. Similar to other records in the system, deviation record 154 can also include attributes reflecting the characteristics of the information in the record (for example, person name, time stamps, sample types, etc.).

Analysis engine 140 can then leverage deviation record 154 to generate person-specific deviation profile 155 indicating how or to what degree the person genetic sequences deviate from the reference differential stings.

Regardless of the type of analysis or result generated (for example, patient instructions 151, population analysis 153, person-specific profile 155, etc.), analysis engine 140 can further configuration output device 190 to present the result. Output device 190 preferably comprises a computing device coupled with analysis engine 140, possibly over network 115. Examples of output device 190 include cell phones, information kiosks, computer terminals at point of care, insurance company computers, printers, imaging devices, genomic browsers, or other types of devices.

Using a system according to the inventive subject matter will therefore typically include a genetic database. As already noted above, it should be appreciated that the genetic database may be physically located on a single computer, however, distributed databases are also deemed suitable for use herein. Moreover, it should also be appreciated that the particular format of the database is not limiting to the inventive subject matter so long as such database is capable of storing and retrieval of first and second genetic sequence strings representing respective first and second tissues, wherein the first and second sequence strings have a plurality of corresponding sub-strings.

Likewise, it should be noted that the particular format of the first and second genetic sequence strings is not limiting to the inventive subject matter so long as first and second genetic sequence strings will include one or more corresponding sub-strings for which the location in a genome is known. Therefore, suitable data formats will include simple ASCII or binary code, and the sequence strings may be formatted following specifications commonly employed in currently known sequence analytic tools. Therefore, especially preferred formats include EMBL, GCG, fasta, SwissProt, GenBank, PIR, ABI, and SAM/BAM format.

Analysis

Depending on the particular nature of analysis and samples, the type of genetic sequence strings may vary considerably, and it should be pointed out that the sequences may be nucleic acid sequences (DNA or RNA) as well as protein sequences. Most typically, however, the genetic sequence strings will be nucleic acid strings that will represent significant portions of the genome, transcriptome, and/or proteome of the first and second tissues under analysis. For example, it is contemplated that the first and second genetic sequence strings represent at least 10%, more typically at least 25%, more typically at least 50%, even more typically at least 70%, and most typically at least 90% or even substantially the entire (at least 98%) genome, transcriptome, or proteome of the first and second tissues. Thus, it should be appreciated that the systems and methods presented herein will allow for a rapid and highly comprehensive overview of significant differences between first and second tissues while producing a compact and informative output file.

Depending on the type of tissue under investigation, it should be noted that multiple types of analyses can be performed. For example, where the first and second tissues originate from the same biological entity, healthy tissue may be compared against a different healthy tissue or healthy tissue may be compared against a corresponding diseased tissue (for example, tumor tissue). Thus, the biological entity may be a healthy individual or an individual diagnosed with a disease or disorder. On the other hand, where first and second tissues are derived from a cell line (immortalized or primary), genetic effects or epigenetic effects of drugs may be rapidly identified. Similarly, where the first and second tissues are derived from a stem cell, changes in genetic composition or genetic plasticity of the developing embryo may be analyzed. In still further contemplated examples, the first and second tissue may be of an experimental animal model to investigate progression of a disease or effect of a treatment. Alternatively, first and second tissue may even be from a yeast, recombinant bacterial cell, and/or a virus.

Consequently, it should be recognized that the nature of the corresponding sub-strings will vary considerably and will at least in part depend on the type of tissue sampled and on the amount of genomic coverage. However, it is typically preferred that the genomic coverage is relatively high and that in most cases the entire genome is analyzed. Thus, corresponding sub-strings will typically include homozygous and heterozygous alleles.

Regardless of the type of sub-strings, it is generally preferred synchronizing will include a step of aligning at least one of the plurality of sub-strings based on an a priori known location within the first string. As numerous genomes for various organisms (and especially human) are already substantially completely annotated and as even unknown sequences are often annotated with at least a putative function, and as substantially the (linear) sequence entire genomes are known, the number of a priori known locations with respect to a reference genome is high. Thus, knowledge of annotations within the reference genome will serve as a roadmap for effective and accurate synchronization. Of course, it should be appreciated that the nature of the reference genome is not necessarily limited to a genome of a single healthy tissue, but that the reference genome may be any defined (actual or calculated) genomic structure. For example, the reference genome may be constructed from a (typically single tissue of a) plurality of healthy individuals to so generate a consensus reference sequence. Alternatively, the reference string may be based on a consensus of multiple tissues of the same (or different) individual, or on a consensus of diseased tissue samples (from the same or multiple patient).

Consequently, it should be recognized that the differential genetic sequence object will provide information of one or more sample tissue(s) relative to a reference tissue. Thus, and depending on the choice of the reference string, the information content for the differential genetic sequence object may vary considerably. For example, the differential genetic sequence object may provide information that the sample is a match for a particular sub-population (as defined by the reference string) or that the sample has a plurality of mis-matches that may or may not be associated with a disease or condition.

In further preferred aspects of the inventive subject matter, the synchronization may also be performed by aligning the sub-string(s) within a window having a length of less than a length of the at least one of the plurality of sub-strings. Most preferably, synchronization is performed by iteratively and incrementally synchronizing the first and second sequence strings throughout the entire length of the first sequence string. Viewed from a different perspective, synchronizing will thus be performed in a manner similar than that of a zipper in which the two halves are incrementally matched up to produce an alignment. Using the same image, only mis-matched portions of the closed zipper are then reflected in the differential genetic sequence object.

Consequently, it should thus be recognized that the differential genetic sequence object will represent one or more local differential strings, typically at least for a defined portion of the genome (for example, at least one chromosome), and more typically for substantially the entire genome of the first or second tissue. Of course, it should be noted that based on the already known position and/or determined deviation from the reference string, the differential genetic sequence object will typically include one or more attributes with metadata describing the differential genetic sequence object. For example, the attribute may be descriptive of a state of the first and/or second tissues. Where the state is a physiological state, the metadata may reflect neoplastic growth, apoptosis, state of differentiation, tissue age, and/or responsiveness to treatment for the tissue. On the other hand, where the state is a genetic status, the metadata may reflect ploidy, gene copy number, repeat copy number, inversion, deletion, insertion of viral genes, somatic mutation, germline mutation, structural rearrangement, transposition, and/or loss of heterozygosity. Similarly, the state may include pathway model information that is associated with a signaling pathway within the tissues (for example, anticipated responsiveness to drugs, defects in receptors, etc.), and especially contemplated pathways include signaling pathways (for example, growth factor signaling pathway, transcription factor signaling pathway, apoptosis pathway, cell cycle pathway, hormone response pathway, etc.).

Output information provided by the systems and methods presented herein may be in form of a single differential genetic sequence object indicating multiple deviations from the reference string, or more than one differential genetic sequence object indicating individual deviations from the reference string, or any reasonable combination thereof. Most typically, the differential genetic sequence object will be in electronic format, and thus be retrieved and/or transferred as a computer readable file. As will be readily recognized the file is most preferably standardized, and it is especially preferred that the format conforms to a SAM/BAM format.

In light of the above, it should thus be appreciated that the differential genetic sequence object may be used in a variety of manners, and that the differential genetic sequence object is especially suitable for numerous applications in healthcare, population analysis, and personalized medicine.

For example, where one or more differential genetic sequence objects are known for an individual, a patient-specific data set may be produced that is based on a local differential string or on a constellation of multiple local differential strings in the differential genetic sequence object for the patient, and the patient-specific data set is then used to produce a patient-specific instruction. In a typical example, the inventors contemplate a method of providing a health care service in which an analysis engine is coupled to a medical records storage device that stores a differential genetic sequence object for a patient. The analysis engine will then generate patient-specific data using one or more local differential strings or a constellation of a plurality of local differential strings in the differential genetic sequence object for the patient, and produce a patient-specific instruction based on the patient-specific data set.

It should be appreciated that the medical records storage device may be configured in numerous manners and may be portable by the patient (for example, smart-card carried by the patient), accessible by the patient (for example, via smart phone), or remotely stored on a server that is accessible by the patient or medical professional of the patient. As can be taken from the discussion above, the differential genetic sequence object for the patient may include any number of local differential strings (i.e., sequence deviations at a specific position in the genome relative to a reference genome), and the local differential strings may be located in a defined area of the genome, on or more chromosomes, or even in throughout the entire genome. Similarly, the differential genetic sequence object may comprises multiple local differential strings that represent at least two tissue types (for example, healthy versus diseased), or at least two temporally spaced results for the same tissue (for example, prior to treatment with a particular drug at a particular regimen and after treatment commences).

Thus, and viewed from a different perspective, it should be noted that medically relevant information for the entire genome (or a fraction thereof [for example, chromosome or contiguous sequence stretch]) can be expressed as a deviation record having one or more local differential strings, and that the information can be used to compare against a database that contains treatment options, diagnoses, and/or prognoses associated with or for the local differential string. Where multiple local differential strings are present, it is noted that the combination of selected local differential strings may be indicative of a condition, predisposition, or disease, and that such constellation of multiple specific local differential strings may be used to generate the patient-specific data, which is then used to generate the patient-specific instruction. Thus, the nature of the patient-specific instruction will vary considerably, and may be a diagnosis, a prognosis, a prediction of treatment outcome, a recommendation for a treatment strategy, and/or a prescription.

In yet another preferred use of contemplated differential genetic sequence objects, the inventors discovered that genetic analysis is possible not only for individuals, but that also population-wide analyses can be conducted in a rapid and effective manner using the systems and methods presented herein. For example, in a method of analyzing a population, a plurality of differential genetic sequence objects (for example, for a plurality of individuals) are stored in a medical records database of a population, and an analysis engine will identify a constellation of a plurality of local differential strings (for example, based on polymorphisms, epigenetic changes, etc.) within the plurality of differential genetic sequence objects to produce a constellation record, which is then used to generate a population analysis record.

For example, the constellation record can be prepared for blood relatives, members of the same ethnic group or race, a population working in the same occupation, a population living in a selected geographic location. Alternatively, the population may also be defined by having members that share exposure to a pathogen or noxious agent, health history, treatment history, treatment success, gender, species, and/or age. Thus, it should be recognized that the constellation record is a genome-wide analytic tool that will allow identification of individuals as belonging to one or more specific groups as defined by the constellation record. Thus, the constellation record and associated methods may be useful to determine paternity or maternity, or may be useful to generate a patient-specific record in view of the constellation record. For example, the patient-specific record may reveal predisposition to a disease or condition, or sensitivity to certain drugs or other agents. Consequently, the patient-specific record may present a risk assessment and/or an identification of the patient as belonging to a specified population. Alternatively, the patient-specific record may include a diagnosis, a prognosis, a prediction of treatment outcome, a recommendation for a treatment strategy, and/or a prescription that is typically at least in part based on a comparison of the constellation record of the patient with a population analysis record.

In a still further preferred use of contemplated differential genetic sequence objects, a reference differential genetic sequence object is generated (for example, as a consensus record as described above) and stored in a database. A deviation between a plurality of local differential strings in the differential genetic sequence object of a person and a plurality of local differential strings in the reference differential genetic sequence object is then determined to so produce an individual deviation record for that person, which can the be used to generate a person-specific deviation profile. Thus, instead of using one or more physiological parameters (for example, common CBC ordered by a physician), a differential genetic sequence object for (preferably) the entire genome of a person is compared to a reference differential genetic sequence object to so arrive at a significantly more comprehensive collection of information. Most typically, the person-specific deviation profile is then matched against normal or reference records for reference differential genetic sequence objects to so accurately and quickly identify the person as matching a specific condition or disease.

Viewed from a different perspective, it should therefore be appreciated that the systems and methods presented herein are particularly useful in the diagnosis or analysis of a disease or condition that is at least in part due to a modification in the genome, transcriptome, and/or proteome. Among other diseases and conditions, especially contemplated diseases and conditions include acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermnatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, akathesia, Alzheimer's disease, amnesia, amyotrophic lateral sclerosis (ALS), ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain, cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and developmental disorders such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, sensorineural hearing loss, and any disorder associated with cell growth and differentiation, embryogenesis, and morphogenesis involving any tissue, organ, or system of a subject, for example, the brain, adrenal gland, kidney, skeletal or reproductive system, and endocrinological disorders such as disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; hyperpituitarism including acromegaly, giantism, and syndrome of inappropriate antidiuretic hormone (ADH) secretion (SIADH); and disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalemia); respiratory disorders such as allergy, asthma, acute and chronic inflammatory lung diseases, ARDS, emphysema, pulmonary congestion and edema, COPD, interstitial lung diseases, and lung cancers; cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

Example Analysis Embodiments

The following discussion relating FIGS. 2-5 provide example embodiments of the analyses discussed above.

Figure 2:
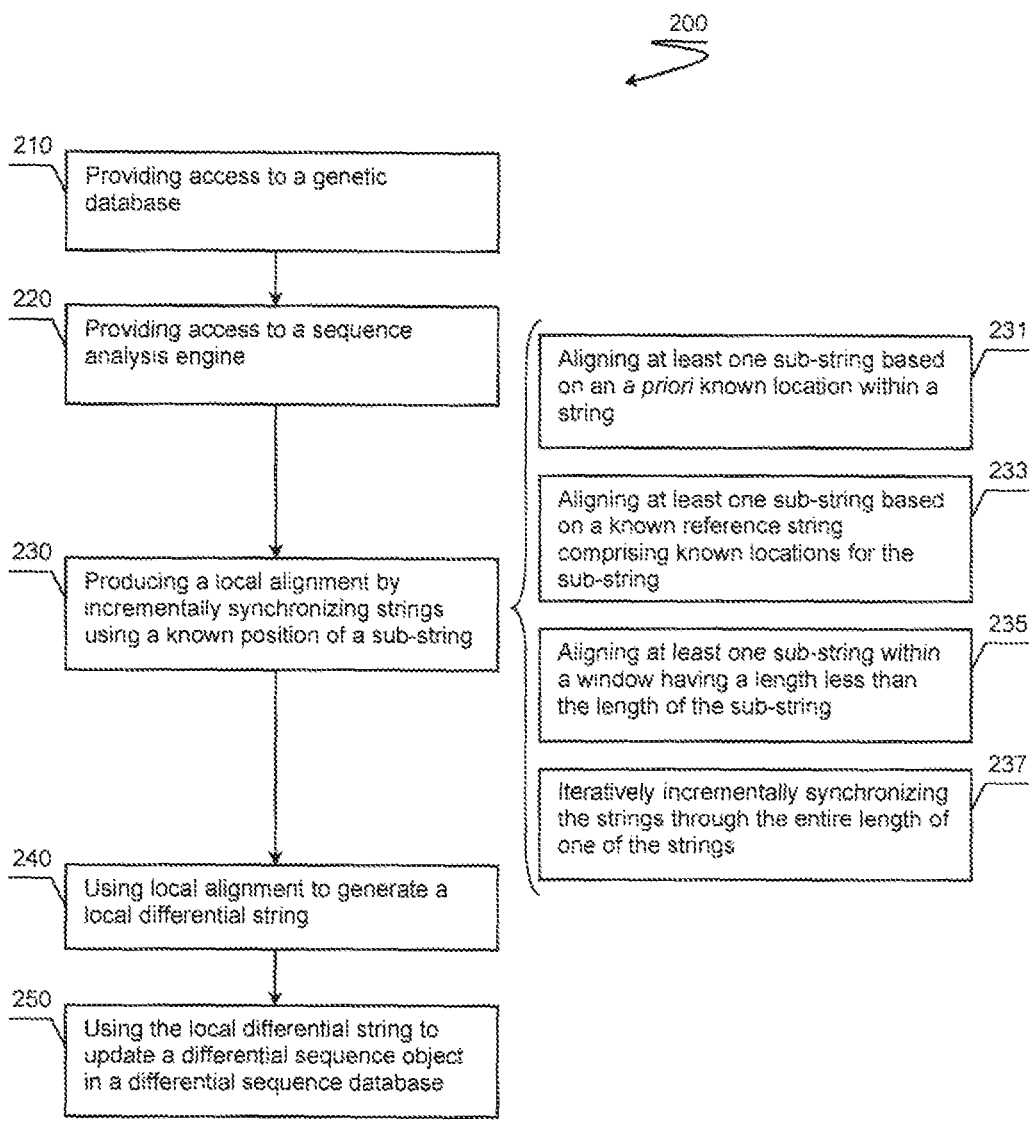
FIG. 2 is a schematic of a method of deriving a differential genetic sequence object.

FIG. 2 illustrates method 200 of deriving a differential genetic sequence object, which can be used for further analyses as discussed above and with respect to FIGS. 3-5. Method 200 begins with step 210 comprising providing access to a genetic database. Preferred genetic databases store at least a first genetic sequence string from a tissue and a second genetic sequence string from a second, possibly different tissue. Each genetic sequence string preferably comprises one or more corresponding sub-strings.

Step 220 includes providing access to a sequence analysis engine coupled with the genetic database, possibly over a network or via one or more Application Program Interfaces (APIs). Step 230 preferably includes the analysis engine producing a local alignment by incrementally synchronizing the first and second genetic sequence strings by using at least one known position of one of the corresponding sub-strings. Producing the local alignment can be done using several techniques. For example, step 231 can include aligning at least one of the sub-strings based on an a priori known location within the one of the genetic sequence strings. Further, step 233 can include aligning the sub-strings based on a known reference string comprising known location for at least one of the sub-string. Still further, step 235 can include aligning the sub-string within a window having a length of less than a length of the sub-string itself. Yet another example includes step 237, which comprises iteratively incrementally synchronizing the genetic sequences strings through the entire length of at least one of the strings.

Regardless of how a local alignment is achieved, method 200 continues at step 240 by the analysis engine using the local alignment to generate a local differential string between the genetic sequence strings within the local alignment. Finally, at step 250 the analysis engine uses the local differential string to update a differential genetic sequence object in a differential sequence database. The differential genetic sequence object can then be used for further review or analysis.

Figure 3:
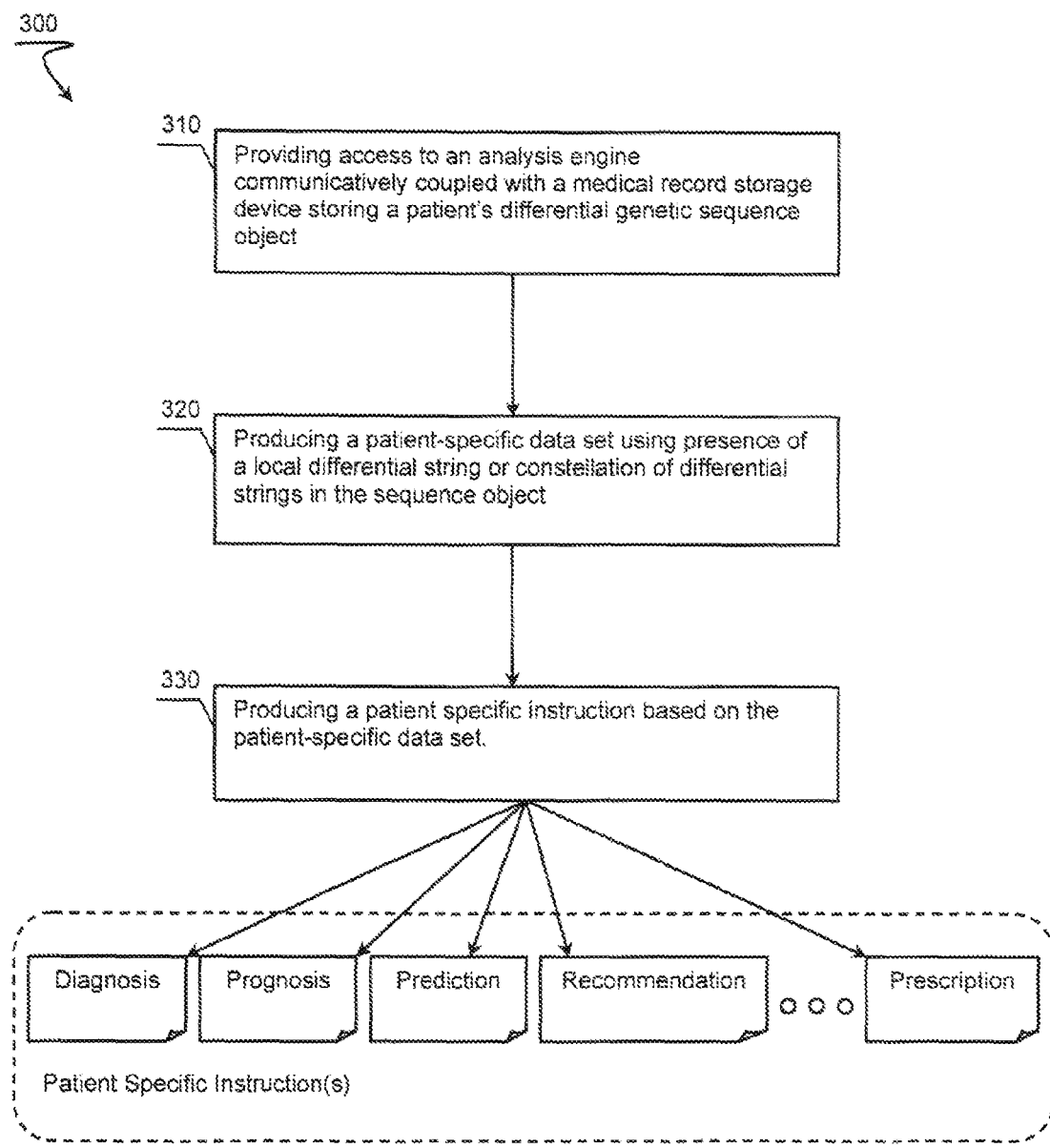
FIG. 3 is a schematic of a method of providing a health care service in the form of patient specific instructions.

FIG. 3, for example, illustrates method 300 of providing a health care service based on a differential genetic sequence object. Step 310 includes providing access to an analysis engine that is informationally coupled with a medical records database comprising a storage device (for example, hard drive, solid state drive, file system, cell phone memory, memory card, etc.). The medical records database preferably stores differential genetic sequence objects for one or more patients.

Step 320 includes the analysis engine producing a patient-specific data set using a presence of a local differential string or constellation of local differential strings in the differential genetic sequence object of the patient. Further, the analysis engine at step 330 produces a patient-specific instruction based on the patient-specific data set. For example, the analysis engine can compare the patient's local differential string attributes within the patient-specific data set to known conditions having similar differential strings. Thus the analysis engine can generate one or more patient-specific instructions possibly including a diagnosis, a prognosis, a prediction of treatment outcome, a recommendation on a treatment strategy, a risk assessment, a prescription, or other type of instructions.

Figure 4:
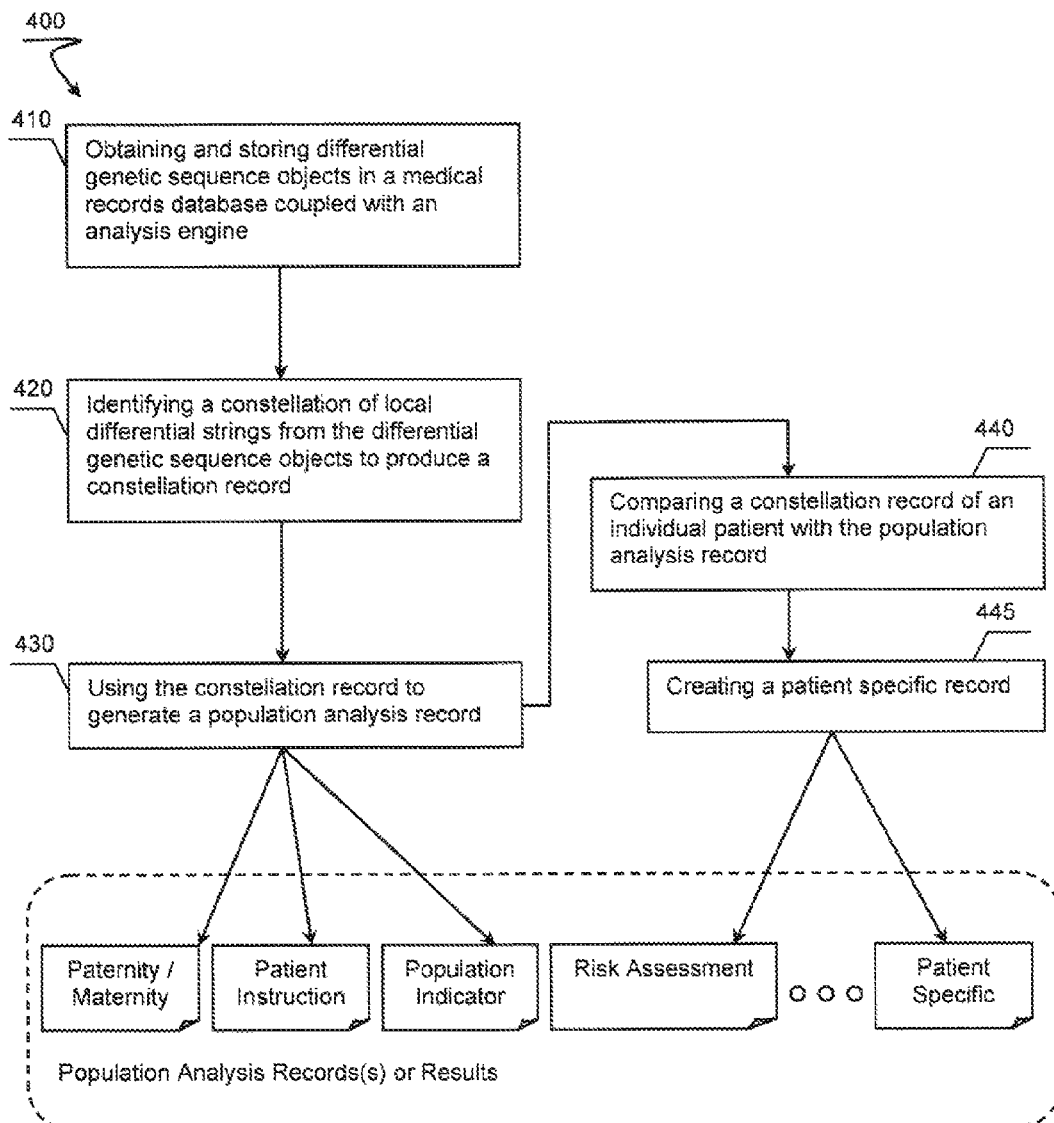
FIG. 4 is a schematic of a method of analyzing a population with respect to differences in genetics.

The differential genetic sequence objects can also be used within method 400 for analyzing a population as illustrated in FIG. 4. Step 410 includes obtaining or storing differential genetic sequence objects in a medical records database where the medical records database stores information across a population of people. One should appreciate that records in the medical records database can be obtained by a queries constructed according to attributes of the population (for example, demographics, ethnicity, illnesses, geography, working conditions, exposures, etc.). For example, a result set of differential genetic sequence objects can be generated by submitting a query targeting all males living in a zip code of European descent. Preferably the medical records database is communicatively coupled with an analysis engine.

Step 420 includes the analysis engine identifying a constellation of local differential strings within multiple differential genetic sequence objects. For example, the constellation could include local differential strings for a specific population of individuals, perhaps individuals who visited the same geographic region. The analysis engine further produces a constellation record comprising information about the constellation.

Step 430 can include the analysis engine using the constellation record to generate a population analysis record, which can be presented on one or more output devices. Example population analysis records could include paternity or maternity confirmation, ancestry information, population indicators, or other population information.

In some embodiments, method 400 includes step 440 where the analysis engine compares a constellation record of an individual patient derived from patient related differential genetic sequence objects within the medical records database to one or more generated population analysis records. Thus a patient's genetic status can be compared against a "normalized" population. Further, at step 445, the analysis engine can create a patient-specific record from the information. For example, the patient specific record could include risk assessment of the patient falling within a specific population, or could include patient instructions as discussed previously.

Figure 5:
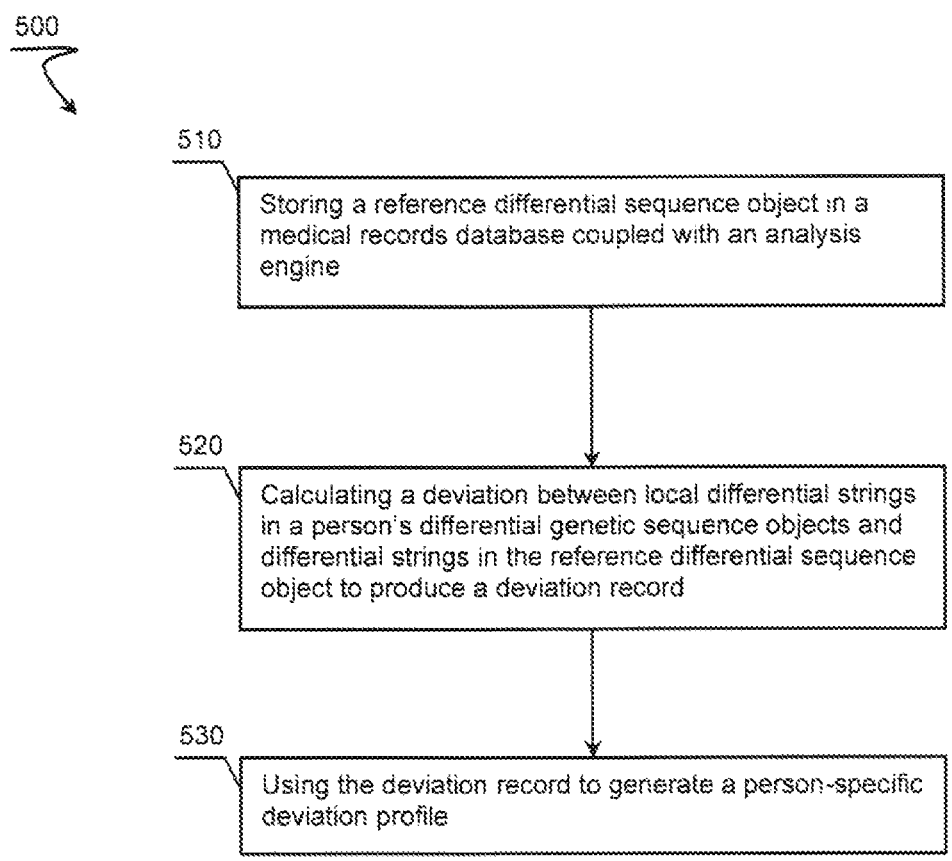
FIG. 5 is a schematic of a method of analyzing a differential genetic sequence object of a person.

Another use of differential genetic sequence objects is represented by method 500 of FIG. 5. Method 500 represents using differential genetic sequence objects of a person to derive a person-specific deviation profile relative to a known reference. Step 510 include storing a reference differential genetic sequence object in a medical records database, which is communicatively coupled with an analysis engine. The reference differential genetic sequence object could be a statistical average over a population or population segment, a canonical person, another person, or other type of references.

Step 520 includes the analysis engine calculating a deviation between one or more of a person's differential genetic sequence objects and at least one reference differential genetic sequence object. The analysis engine can further convert the deviation into a deviation record comprising attributes describing the deviation. One should appreciate a deviation record could include information related to one or more dimensions of deviations (for example, number of difference, length of differences, etc.).

At step 530 the analysis engine uses the deviation record to generate a person-specific deviation profile. The analysis engine can further configure one or more computing devices to present the profile according to a desirable format. In some embodiments, the deviation profile can be presented to the person in graphical manner that is easy to read for a lay person, while the information presented can be more complex when presented to a geneticist, doctor, insurance company, or other entity.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A processor-based method of deriving a differential genetic sequence object, the method comprising:
   providing access to a genetic database storing (a) a first genetic sequence string representing a first tissue and (b) a second genetic sequence string representing a second tissue, wherein the first and second sequence strings have a plurality of corresponding sub-strings;
   providing access to a sequence analysis engine coupled with the genetic database; producing, using the sequence analysis engine, a local alignment using a known position of at least one of a plurality of corresponding sub-strings;
   determining base probabilities of possible locations of sequence reads in the first and second genetic sequence strings as a function of error rates of at least one sequencer;
   identifying a difference between the first set and the second set of genetic sequence strings by comparing genotypes from the first and the second sets that, overlapping at a particular genomic position, maximize a likelihood probability function identifying the genotypes as being different and that are located at the particular genomic position, where the likelihood probability function operates as a probability distribution of a likelihood that unmapped sequence reads of both the first set, representing the first tissue, and the second set, representing the second tissue, align to possible junction sequences, modeled over the base probabilities and associated sequence reads;

using the local alignment and the identifying the difference to generate a local differential string between the first and second sequence strings within the local alignment; and using, by the sequence analysis engine, the local differential string to update a differential genetic sequence object in a differential sequence database with information according to the local differential string; and generating a patient specific clinical instruction based on the information of the differential genetic sequence object.

2. The method of claim 1 wherein the first and second genetic sequence strings represent at least 10% of a genome, transcriptome, or proteome of the first and second tissues, respectively.

3. The method of claim 1 wherein the first and second genetic sequence strings represent at least 50% of a genome, transcriptome, or proteome of the first and second tissues, respectively.

4. The method of claim 1 wherein the first and second genetic sequence strings represent substantially the entire genome, transcriptome, or proteome of the first and second tissues, respectively.

5. The method of claim 1 wherein the first and second tissues originate from the same biological entity, the biological entity selected from the group consisting of a patient, a healthy individual, a cell line, a stem cell, an experimental animal model, a recombinant bacterial cell, and a virus.

6. The method of claim 1 wherein the first tissue is a healthy tissue and wherein the second is a diseased tissue.

7. The method of claim 6 wherein the diseased tissue comprises a tumor tissue.

8. The method of claim 1 wherein the corresponding sub-strings comprise homozygous alleles.

9. The method of claim 1 wherein the corresponding sub-strings comprise heterozygous alleles.

10. The method of claim 1 wherein the step of synchronizing comprises aligning at least one of the plurality of sub-strings is based on an a priori known location within the first string.

11. The method of claim 1 wherein the step of synchronizing comprises aligning at least one of the plurality of sub-strings based on a known reference string comprising known locations for the at least one of the plurality of sub-strings.

12. The method of claim 11 wherein the known reference string is a consensus sequence.

13. The method of claim 1 wherein the step of synchronizing comprises aligning the at least one of the plurality of sub-strings within a window having a length of less than a length of the at least one of the plurality of sub-strings.

14. The method of claim 1 further comprising iteratively incrementally synchronizing the first and second sequence strings throughout the entire length of the first sequence string.

15. The method of claim 1 wherein the differential genetic sequence object represents a plurality of local differential strings for at least one chromosome.

16. The method of claim 1 wherein the differential genetic sequence object represents a plurality of local differential strings for substantially the entire genome of the first tissue.

17. The method of claim 1 wherein the differential genetic sequence object comprises an attribute comprising metadata describing the differential genetic sequence object.

18. The method of claim 17 wherein the attribute comprises a state of at least one of the first and second tissues.

19. The method of claim 18 wherein the state comprises a physiological state of at least one of the first and second tissues.

20. The method of claim 19 wherein the physiological state comprises a state selected from the group consisting of neoplastic growth, apoptosis, state of differentiation, tissue age, and responsiveness to treatment.

21. The method of claim 18 wherein the state comprises genetic status.

22. The method of claim 21 wherein the genetic status comprises a status selected from the group consisting of at least one ploidy, gene copy number, repeat copy number, inversion, deletion, insertion of viral genes, somatic mutation, germline mutation, structural rearrangement, transposition, and loss of heterozygosity.

23. The method of claim 18 wherein the state comprises pathway model information associated with a signaling pathway within the tissues.

24. The method of claim 23 wherein the signaling pathway is selected from the group consisting of a growth factor signaling pathway, a transcription factor signaling pathway, an apoptosis pathway, a cell cycle pathway, and a hormone response pathway.

25. The method of claim 1 wherein the differential genetic sequence object comprises a file.

26. The method of claim 25 wherein the file conforms to a standardized format.

27. The method of claim 26 wherein the file conforms to a SAM/BAM format.

28. The method of claim 1 wherein a patient or person associated with the patient specific clinical instruction is selected from the group consisting of a patient or person diagnosed with a condition, the condition selected from the group consisting of a disease and a disorder.

29. The method of claim 28 wherein the condition is selected from the group consisting of acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, akathesia, Alzheimer's disease, amnesia, amyotrophic lateral sclerosis (ALS), ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

30. The method of claim 28 wherein the condition is selected from the group consisting of cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders including acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and developmental disorders including renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies including Charcot-Marie-Tooth disease and neurofibromatosis, hypothyroidism, hydrocephalus, seizure disorders including s Syndenham's chorea and cerebral palsy, spina bifida, anencephaly, craniorachischisis, congenital glaucoma, cataract, sensorineural hearing loss, and any disorder associated with cell growth and differentiation, embryogenesis, and morphogenesis involving any tissue, organ, or system of a subject, for example, the brain, adrenal gland, kidney, skeletal or reproductive system.

31. The method of claim 28 wherein the condition is selected from the group consisting of endocrinological disorders including disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; hyperpituitarism including acromegaly, giantism, and syndrome of inappropriate antidiuretic hormone (ADH) secretion (SIADH); and disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalemia); respiratory disorders including allergy, asthma, acute and chronic inflammatory lung diseases, ARDS, emphysema, pulmonary congestion and edema, COPD, interstitial lung diseases, and lung cancers; cancer including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders including acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

* * * * *